United States Patent [19]

Boisde et al.

[11] 4,188,126
[45] Feb. 12, 1980

[54] PHOTOMETER WITH CONCAVE MIRRORS AND FIELD OPTICS

[75] Inventors: Gilbert Boisdé, Bures sur Yvette; Alain Boissier, Orsay, both of France

[73] Assignee: Commissariat a l'Energie Atomique, Paris, France

[21] Appl. No.: 905,344

[22] Filed: May 12, 1978

[30] Foreign Application Priority Data

May 13, 1977 [FR] France .................. 77 14753

[51] Int. Cl.² .................... G01N 21/24; G01J 1/42
[52] U.S. Cl. .................... 356/440; 250/576; 350/294; 356/246
[58] Field of Search ........... 250/343, 576; 350/294; 356/246, 436, 437, 438, 439, 440, 441, 442, 301

[56] References Cited

U.S. PATENT DOCUMENTS

| | | | |
|---|---|---|---|
| 2,779,230 | 1/1957 | White | 350/202 |
| 3,436,665 | 4/1969 | Rigrod | 350/294 |
| 3,469,920 | 9/1969 | Dumartin et al. | 356/246 |
| 3,518,001 | 6/1970 | Hell | 356/300 |
| 3,524,066 | 8/1970 | Blakkan | 356/246 |
| 3,531,204 | 9/1970 | Holland et al. | 356/352 |
| 3,861,809 | 1/1975 | Hall | 356/246 |

FOREIGN PATENT DOCUMENTS 1042722 11/1953 France .................. 356/442

Primary Examiner—John K. Corbin
Assistant Examiner—R. A. Rosenberger

[57] ABSTRACT

Photometer of the type comprising two facing mirrors, means for introducing a light beam between said mirrors, extraction means for said light beam after multiple reflections on the mirrors and means for introducing a fluid to be measured between these mirrors, wherein the two mirrors are concave mirrors, whose centers of curvature are slightly staggered relative to one another and wherein it comprises a field optics by transmission disposed in the vicinity of the centers and which optically conjugates the mirrors, the light beam introduction means comprising a first optical system having an exit pupil in the vicinity of the field optics, the extraction means of the light beam comprising a second optical system having an entrance pupil in the vicinity of the field optics, said entrance and exit pupils being optically conjugated by the action of the multiple reflections on the mirrors.

Particular applications of the photometer are to the measurement of the turbidity of nuclear reactor and river waters or to the detection of pollutants in liquids or gases.

10 Claims, 6 Drawing Figures

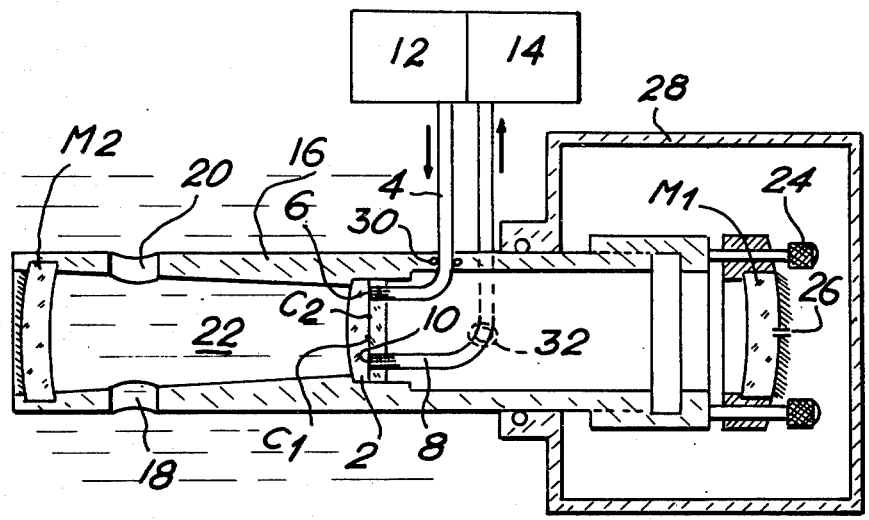
FIG. 1
FIG. 2
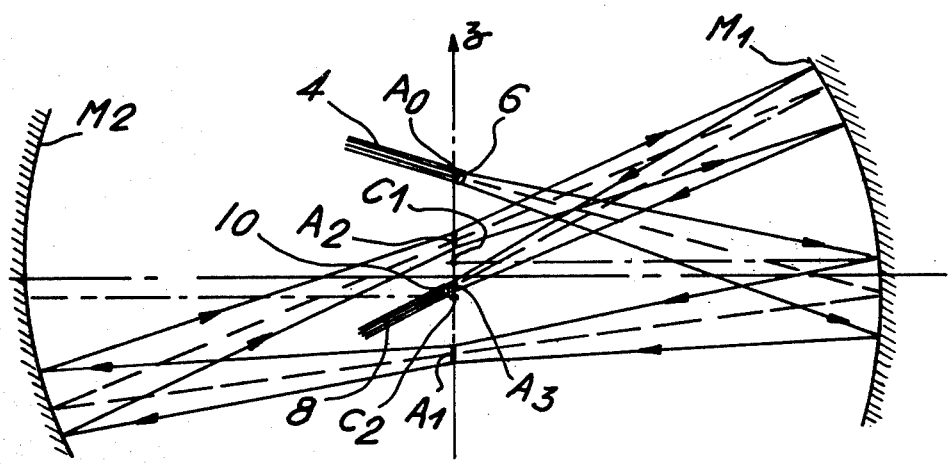

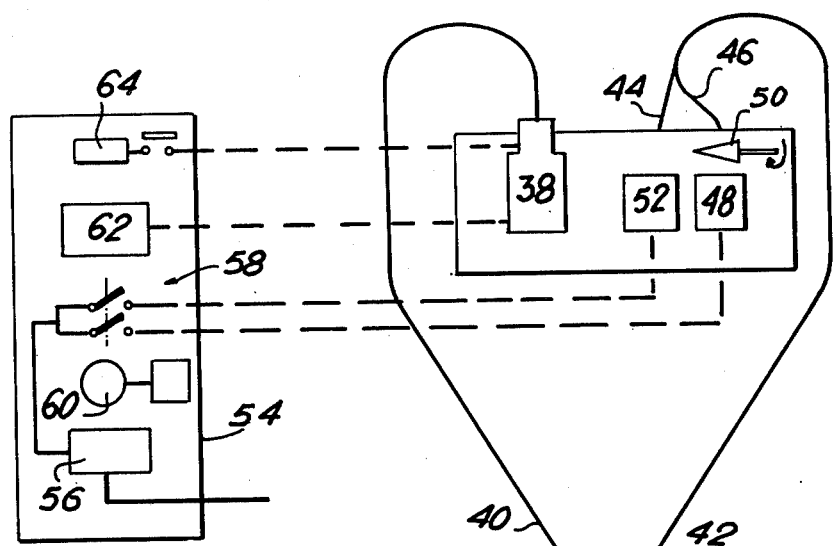
FIG.6
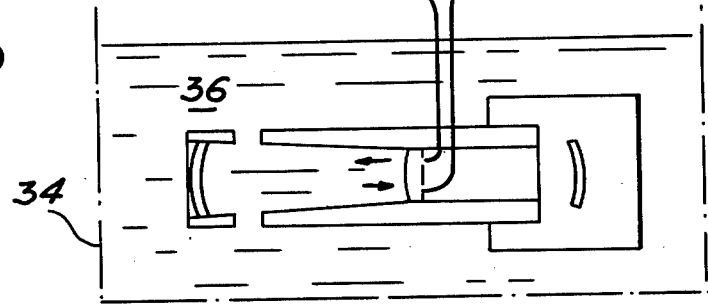
FIG.5
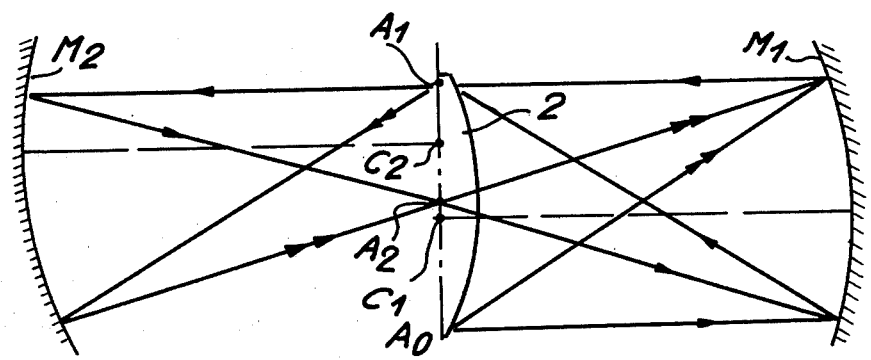

PHOTOMETER WITH CONCAVE MIRRORS AND FIELD OPTICS

BACKGROUND OF THE INVENTION

The present invention relates to a photometric device. It is used in the measurement of the optical density of fluids (for example liquids) and in particular the measurement of the turbidity of the waters of rivers or nuclear reactors, as well as for the detection of pollutants in liquids or gases.

Photometers are known which comprise a cell containing a volume of fluid to be analysed and optical means for making a light beam pass through said cell. The measurement of the attenuation due to the passage through the vessel makes it possible to calculate the optical density of the fluid and the concentration of one of the substances present in the fluid.

Although such photometers are suitable in certain cases, they have the disadvantage of offering the light beam only a short path which limits their precision. Therefore, photometers have been proposed which have two generally plane mirrors disposed on either side of the vessel in such a way that the light beam can pass to and fro between the mirrors, the optical path being lengthened for the same overall dimensions.

BRIEF SUMMARY OF THE INVENTION

The photometer according to the present invention is of the latter type, but it has much better performance characteristics with respect to the precision of measurement which it makes possible, because the optical means which it uses are such that the light beam path in the fluid to be analysed is much longer than in the prior art photometers. For example, this path is approximately one meter in the case of a cell whose length is about 10 cm, with a distance between the mirrors of approximately twenty centimeters.

This result is obtained because the number of reflections of the light beam on the mirrors can be large in the present invention and for example approximately 10. In the prior art photometers, this number is necessarily limited to 3 or 4 because beyond this number the light beam deviates from the axis of the apparatus at a point such that it can no longer strike the reflecting mirrors. Moreover, as these mirrors are planar, the cross-section of the beam widens to a considerable extent, which does not permit the detection under good conditions of the light leaving the cell.

To obviate these disadvantages, the present invention uses on the one hand concave mirrors whose centres of curvature are slightly staggered relative to one another and on the other hand a field lens disposed in the vicinity of said centres and which optically conjugates the two mirrors.

The measuring light beam is introduced at the field lens by an optical system whose exit pupil is located in the vicinity of the field lens, i.e. the vicinity of the centres of curvature. It is known from the standard laws of optics that the image of an object point located in the vicinity of the centre of curvature of a spherical mirror is an image point such that said centre of curvature is as a first approximation the centre of the segment formed by the object point and the image point. The exit pupil of the entrance optical system thus gives, after a first reflection in one of the mirrors, an image which in turn gives by reflection on the second mirror a second image which is symmetrical to the first with respect to the centre of curvature of the second mirror and so on. Thus, as a result of the multiple reflections on the mirrors, a sequence of different images is obtained, the latter being essentially located in the plane containing the centres of curvature. An exit optical system is then arranged in such a way that its entrance pupil coincides with one of these images. In other words, the entrance and exit pupils of the entrance and exit optical systems respectively are optically conjugated by the mirrors after a random but predetermined number of reflections. The function of the field optics is to prevent the light rays straying too far from the axis of the system.

Due to the use of said field optics and to the conjugation of the entrance and exit pupils, the number of reflections can be increased which lengthens the path in the analysis cell, whilst the extraction of the light energy on leaving the photometer is performed under excellent conditions despite the length of said path. Thus, as a result of these two characteristics, the photometer according to the invention has an excellent sensitivity which was not provided by any of the prior art photometers.

More specifically, the present invention relates to a photometer of the type comprising two facing mirrors, means for introducing a light beam between said mirrors, extraction means for said light beam after multiple reflections on the mirrors and means for introducing a fluid to be measured between these mirrors, wherein the two mirrors are concave mirrors, whose centres of curvature are slightly staggered relative to one another and wherein it comprises a field optics by transmission disposed in the vicinity of the centres and which optically conjugates the mirrors, the light beam introduction means comprising a first optical system having an exit pupil in the vicinity of the field optics, the extraction means of the light beam comprising a second optical system having an entrance pupil in the vicinity of the field optics, said entrance and exit pupils being optically conjugated by the action of the multiple reflections on the mirrors.

The term "slightly staggered centres of curvature" is understood to mean centres which are spaced from one another by a limited distance compared with the radii of curvature of the mirrors and for example less than a tenth of said rays in such a way that the optical system functions in a Gaussian approximation.

Although any optical system ables to introduce a light beam between two mirrors or to extract the same may be suitable (for example systems having prisms or lenses or systems having a laser and a deflector) preference is given to the use of light guides formed from optical fibre bundles.

BRIEF DESCRIPTION OF THE DRAWINGS

The invention will be explained in greater detail hereinafter relative to preferred non-limitative embodiments and with reference to the attached drawings, wherein show:

FIG. 1 a longitudinal section of the photometer according to the invention.

FIG. 2 an explanatory diagram showing the course of the light beams in the absence of the field optics in a longitudinal plane.

FIG. 5 a diagram showing the course of the light beams in a longitudinal plane, taking account of the field optics.

FIG. 6 a snyoptic diagram of a remote photometric analyser using the photometer according to the invention.

DETAILED DESCRIPTION OF THE PREFERRED EMBODIMENTS

Figure 3:
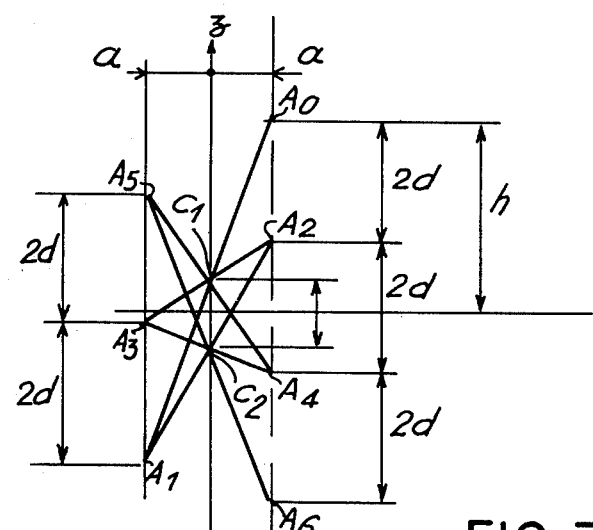
FIG. 3 an explanatory diagram showing the distribution of the various images in the cross-sectional plane containing the centres of curvature.

The photometric device or photometer shown in FIG. 1 comprises two concave mirrors $M_1$ and $M_2$, whose centres of curvature $C_1$ and $C_2$ respectively are slightly staggered relative to one another by a short distance with respect to the radii of curvature of the mirrors. A field optics 2 is disposed in the vicinity of centres $C_1$ and $C_2$ and comprises at least one lens, for example a plano-convex lens. A first optical fibre 4 constitutes means for introducing a beam of light between the mirrors. This fibre has an exit face 6 located in field optics 2. A second optical fibre 8 constitutes means for extracting the light and has an entrance face 10. The faces 6 and 10 of the optical fibres are optically conjugated by multiple reflections on mirrors $M_1$ and $M_2$. This feature will become more readily comprehensible from the following description. During operation, fibre 4 is connected to a light source 12 and fibre 8 to a detector 14.

Means for passing between the mirrors the fluid of which it is desired to measure one of the optical characteristics, for example the absorption are combined with said optical means. These means comprise an envelope 6 sealed at one end by mirror $M_2$ and essentially in its centre by field optics 2. This envelope has two openings 18 and 20 for the entry and exit of the fluid respectively. This fluid is generally but not exclusively a liquid 22.

Mirror $M_2$ is generally fixed relative to the envelope and mirror $M_1$ which is not immersed in liquid 22 is provided with means for regulating its orientation and position. In the illustrated variant, these means comprise regulating screws 24.

Mirror $M_2$ may be constituted by two concentric faces, whereby the outer face which is not in contact with the liquid is covered with a reflecting coating.

Mirror $M_1$ advantageously has a small cutout 26 in its reflecting coating and this is used for checking and optical settings. In certain cases, this cutout may be replaced by an opening made in the mirror.

If it is desired to use the apparatus immersed in a liquid the regulating system of mirror $M_1$ is protected by a sealed box 28 and gaskets 30 and 32 are provided round fibres 4 and 8.

Obviously, in another variant, the enclosure could be sealed by the two mirrors $M_1$ and $M_2$, in which case the liquid would be distributed on either side of the field lens. However, to obviate sealing problems at the movable mirror, preference is generally given to the illustrated variant which makes it possible to form a cell with fixed members.

Figure 4:
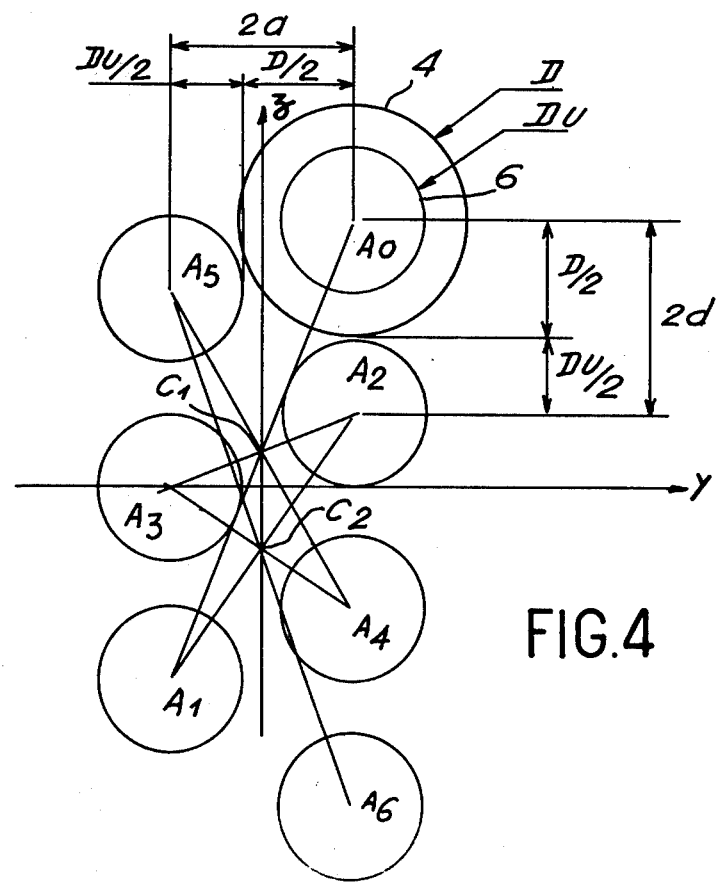
FIG. 4 another diagram showing the dimensions of said images in said cross-sectional plane.

For the purpose of describing the operation of such an apparatus reference should be made to the diagrams of FIGS. 2 to 4 which show the path of the light beams between the mirrors and the distribution of the different images of the entrance pupil of the system.

In order to facilitate the understanding of the operation, it is initially assumed that the field lens (which is normally placed between the mirrors) does not exist. This is the case in FIG. 2 which shows the path of the light beams between the mirrors projected onto a longitudinal plane. This applies in the case where the centres of curvature $C_1$ and $C_2$ of the mirrors are precisely located in the same cross-sectional plane. However, it is obvious that they may be slightly displaced relative to such a plane.

Point $A_0$ represents the entrance pupil of the optical system, i.e. in practice the exit face 6 of light guide 4. According to a known geometrical optical law, the image of point $A_0$ in mirror $M_1$ of centre $C_1$ is a point $A_1$ symmetrical to $A_0$ with respect to $C_1$. The image of $A_1$ in mirror $M_2$ of centre $C_2$ is a point $A_2$ symmetrical to $A_1$ with respect to $C_2$. The image of $A_2$ is located at $A_3$ symmetrical to $A_2$ with respect to $C_1$ and so on for the other images resulting from the other reflections.

According to an essential feature of the invention, the entrance face 10 of fibre 8 coincides with one of these images of exit face 6 of entrance fibre 4. Thus, said face 10 constitutes the exit pupil of the optical system. Thus, exit fibre 8 is disposed in such a way that pupils 6 and 10 are optically conjugated by the action of the multiple reflections.

In FIG. 2, this conjugation takes place after three reflections, but it is obvious that this relatively small number has only been chosen here to simplify the drawing and that in practice it is advantageously much larger because the optical path, i.e. the sensitivity of the apparatus, increases with the number of reflections.

In a cross-sectional plane passing through the centres of curvature (or in the vicinity thereof, as stated hereinbefore) the situation is that represented in FIGS. 3 and 4. In FIG. 3 the object and image points are indicated in a system of axes yoz in which o is the centre of segments $C_1C_2$, whose length is d. The object point $A_0$ has for its coordinates a and h. It is easy to see that the sequence of coordinates of the image points is as follows:

| | |
|---|---|
| -for $A_1$ | $-a$ and $-(d+h)$ |
| -for $A_2$ | $a$ and $2d+h$ |
| -for $A_{2n-1}$ | $-a$ and $-(2n-1)d - h$ |
| -for $A_{2n}$ | $a$ and $2nd + h$ |

The variation between two successive images $A_{2n}$ and $A_{2n+2}$ located on the same side of the line of centres is $2d$. It is desirable that these images are separated in such a way that if D is the overall diameter of the entrance fibre 4 and Du the useful diameter of exit face 6, the following condition must be respected:

$$2d \geq D/2 + Du/2$$

The variation between two successive images $A_{2n}$ and $A_{2n+1}$ located on either side of the line of centres is equal to $2a$. To separate the two images a second condition must be respected which is:

$$2a \geq D/2 + Du/2$$

These two relationships make it possible to determine the lower limit values of d and a knowing the dimensions of the entrance optical fibre. The limit situation which corresponds to equality between the two terms of the above relationships is illustrated by FIG. 3.

As the light beam deviate progressively further from the axis after each reflection, they end up by no longer striking the mirrors in such a way that the number of reflections is limited. In order to increase it and at the same time obtain a very long optical path without having recourse to mirrors with excessive dimensions which would increase the necessary liquid volume, according to the invention a field optics is placed in the vicinity of the centres of curvature. The focal line of said optics is such that mirrors $M_1$ and $M_2$ are optically conjugated. All the spots produced by the different images on the mirrors then coincide, as is shown in FIG. 5.

The number of reflections is now only limited by the degradation of the image on moving away from the centre of curvature of the mirrors and by the dimension of the field lens, which obviously remains finite.

Following this explanation of the operation of the apparatus, it is pointed out that it can be used whatever the optical index of the liquid to be analysed.

For explanatory purposes, the Applicant has realised a photometer with the following characteristics:

| | |
|---|---|
| -internal radius of curvature of mirrors | 100mm |
| -number of reflections | 9 |
| -optical path in the half-cell | 1000mm |
| -diameter of the cell on the fibre side | ≃25mm |
| -diameter of the cell on the mirror side for a | |
| -divergence on leaving the fibre of approx.20° | ≃35mm |
| -external diameter of the fibres | ≃5mm |
| -focal length of the field lens | approx. 50mm |
| -useful diameter of the fibre | ≃3mm |
| -volume of the cell | ≃75cm$^3$ |

The losses in the cell are mainly due to the losses occurring at each reflection on the mirrors, because their coefficient of reflection is below unity and to the losses by reflection on the traversed glass surfaces. The losses by geometrical aberrations and by absorption in glasses can be considered negligible. For each to and fro movement in the cell, there are two reflections on the mirrors and two passages through the glass surfaces. With reflection losses of 5% per mirror and passage losses of 5% (if one of the field lens faces is treated with an antireflection coating), the optical density for a to and fro movement is approximately 0.1. The optical density of the cell is 0.5 for five to and fro movements, i.e. a path of approximately 1 m.

Such a photometer makes it possible to carry out extremely precise turbidity measurements with an excellent reproducibility (correlation coefficient of 0.999). Thus, using such an apparatus it is possible to show a turbidity difference between distilled water taken as 0 and tap water (approx. 0.2 of optical density) or exchange water (approx. 0.05 of optical density).

One example of the use of the apparatus is the measurement of the turbidity of nuclear reactor and river waters. In the former case, it is pointed out that the sensitivity limit with magnetite is approx. one part per milliard.

Another example is the measurement of the uranium concentration of a solution. Using a cell with a 5 cm optical path (as in prior art apparatus) a sensitivity limit of approx. 0.1 g/l$^{-1}$ is obtained for 0.02 of optical density. With the present apparatus, the following results are obtained:

| | | |
|---|---|---|
| - solution 0.15g.l$^{-1}$ | Measured optical density 0.635 | |
| - dilution 1/2, i.e.0.075g.l$^{-1}$ | | 0.325 |
| 1/4, i.e.37.5 mg.l$^{-1}$ | | 0.172 |
| 1/8, i.e. 18.75 mg.l$^{-1}$ | | 0.088 |
| - dilution 1/16,i.e. 9.37 mg.l$^{-1}$ | | 0.040 |
| 1/32,i.e. 4.68 mg.l$^{-1}$ | | 0.018 |
| 1/64,i.e. 2.34 mg.l$^{-1}$ | | 0.002 |

The same apparatus equipped with 1 meter long optical fibres illuminated by a 4 milliwatt helium-neon laser makes it possible to measure traces of nickel in a solution, although the nickel absorption peak is displaced relative to the laser wave length.

FIG. 6 shows a diagram of a remote photometric analyser using the apparatus according to the invention. The apparatus 34 is immersed in the liquid 36 to be analysed. It is energised by the light source 38 connected to the apparatus 34 by an optical fibre 40. The light return takes place by a fibre 42 which is subdivided into two bundles of fibres 44, 46. A first detector 48, set on the absorption peak of the substance to be detected, receives the light transmitted by fibre 46 through an optical wedge 50. A second detector 52, set to the valley of the absorption curve, receives the light transmitted by fibre 44. Wedge 50 serves to balance the two detection paths. The signal supplied by detectors 48 and 52 are passed by the connections to a measuring system 54, which in particular comprises a colorimeter 56 receiving one or other of the detection signals through a reversing switch 58, which is controlled by a programmed circuit 60. This system also comprises supply and regulating circuit 62 of light source 38 and a stop-go switch 64. Obviously, the system described generally functions in absorption, but it can also function in light diffusion and with any fluid, which can obviously be liquid, but also gaseous.

The invention is not limited to the embodiments described and represented hereinbefore and various modifications can be made thereto without passing beyond the scope of the invention.

What is claimed is:

1. A photometer of the type comprising two facing mirrors, means for introducing a light beam between said mirrors, extraction means for said light beam after multiple reflections on the mirrors and means for introducing a fluid to be measured between these mirrors, wherein the two mirrors are concave mirrors, whose centres of curvature are slightly staggered relative to one another and wherein it comprises a field optics by transmission disposed in the vicinity of the centres and which optically conjugates the mirrors, the light beam introduction means comprising a first optical system having an exit pupil in the vicinity of the field optics, the extraction means of the light beam comprising a second optical system having an entrance pupil in the vicinity of the field optics, said entrance and exit pupils being optically conjugated by the action of the multiple reflections on the mirrors.

2. A photometer according to claim 1, wherein the said first and second optical systems, comprise light guides specifically by optical fibres, said guides having exit and entrance faces coinciding with said exit and entrance pupils.

3. A photometer according to claim 1, wherein the means for introducing a fluid between the mirrors comprising a cell constituted by an envelope sealed at one end by one of the mirrors and in its centre by the field optics, said envelope being provided with a fluid supply pipe and a fluid discharge pipe.

4. A photometer according to claim 3, wherein the mirror sealing the cell is constituted by a transparent strip with two concentric faces, the outer face being coated with a reflecting coating.

5. A photometer according to claim 3, wherein the mirror sealing the cell is fixed relative to the photometer.

6. A photometer according to claim 3, wherein the mirror which does not belong with the cell is provided with means for regulating the orientation and position.

7. A photometer according to claim 6, wherein the mirror comprises a small cutout or an opening in its reflecting coating and which is used for regulating the cell.

8. A photometer according to claim 1, wherein the means for introducing a fluid between the mirrors comprise a cell constituted by an envelope sealed at its two ends by two mirrors, said envelope being provided with a fluid supply pipe and a fluid discharge pipe.

9. A photometer according to claim 3, wherein the said pipes are constituted by openings made in the envelope, whereby the photometer can then function when immersed.

10. A photometer according to claim 1, wherein the field optics comprises at least one lens.

* * * * *